United States Patent
Ferris, Jr.

(10) Patent No.: US 9,211,252 B2
(45) Date of Patent: Dec. 15, 2015

(54) INCREASED DRUG LOADING CAPACITY OF POLYMERIC MATERIAL

(75) Inventor: William V. Ferris, Jr., Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1300 days.

(21) Appl. No.: 12/109,494

(22) Filed: Apr. 25, 2008

(65) Prior Publication Data

US 2008/0269175 A1    Oct. 30, 2008

Related U.S. Application Data

(60) Provisional application No. 61/914,344, filed on Apr. 27, 2007.

(51) Int. Cl.
| | |
|---|---|
| *A61K 31/65* | (2006.01) |
| *A61K 47/30* | (2006.01) |
| *A61K 31/497* | (2006.01) |
| *A61K 31/4164* | (2006.01) |
| *A61K 31/192* | (2006.01) |
| *A61P 31/00* | (2006.01) |
| *A61P 29/00* | (2006.01) |
| *A61K 9/00* | (2006.01) |
| *A61K 47/34* | (2006.01) |
| *A61L 27/54* | (2006.01) |
| *A61L 29/16* | (2006.01) |
| *A61L 31/16* | (2006.01) |

(52) U.S. Cl.
CPC .............. *A61K 9/0024* (2013.01); *A61K 47/34* (2013.01); *A61L 27/54* (2013.01); *A61L 29/16* (2013.01); *A61L 31/16* (2013.01); *A61L 2300/406* (2013.01)

(58) Field of Classification Search
CPC .................................................. A61L 2300/406
See application file for complete search history.

(56) References Cited

U.S. PATENT DOCUMENTS

| | | | | |
|---|---|---|---|---|
| 4,612,337 | A  * | 9/1986 | Fox et al. | 514/38 |
| 7,169,404 | B2 * | 1/2007 | Hossainy et al. | 424/423 |
| 2002/0193559 | A1 | 12/2002 | Ford | |
| 2004/0040500 | A1* | 3/2004 | Bouchier et al. | 118/696 |
| 2005/0058835 | A1 | 3/2005 | Howdle | |
| 2006/0078592 | A1 | 4/2006 | Kunzler | |
| 2008/0125728 | A1 | 5/2008 | Bischoff | |

FOREIGN PATENT DOCUMENTS

| | | |
|---|---|---|
| WO | WO 89/04682 | 6/1989 |
| WO | WO 02/47731 | 6/2002 |
| WO | WO 2005/055792 | 6/2005 |

OTHER PUBLICATIONS

John Byers 2003. Solvent Polarity http://www.chemical-ecology.net/java/solvents.htm.*
PCT International Search Report dated Apr. 2, 2009.
Supersaxo et al., Preformed Porous Microspheres for Controlled and Pulsed Release of Macromolecules, Journal of Controlled Release, Elsevier, Amsterda, NL, vol. 23, No. 1, Feb. 1, 1993.
Anonymous: Product Information: n-Butyl Acetate, Internet Article (online), Oct. 2002, p. 1, XP002520870.

* cited by examiner

*Primary Examiner* — Scott Long
*Assistant Examiner* — Sarah Alawadi
(74) *Attorney, Agent, or Firm* — Mueting, Raasch & Gebhardt, P.A.

(57) ABSTRACT

A method includes (i) contacting a polymeric material with a first solvent to produce a pre-extracted polymeric material, and (ii) contacting the pre-extracted material with a solution comprising one or more therapeutic agents and a second solvent to incorporate the therapeutic agents into the pre-extracted polymeric material. The first or second solvents are the same or different.

12 Claims, 3 Drawing Sheets

INCREASED DRUG LOADING CAPACITY OF POLYMERIC MATERIAL

RELATED APPLICATION

This application claims the benefit of Provisional Application No. 60/914,344, filed on Apr. 27, 2008, which application is hereby incorporated herein by reference in its entirety.

FIELD

This disclosure relates, inter alia, to implantable medical devices, polymeric materials, and therapeutic agents. More particularly, it relates to systems, devices and methods for incorporating therapeutic agents into polymeric materials that form a part of or may be disposed in proximity to implantable medical devices.

BACKGROUND

Drugs are loaded into a variety of polymeric materials, which may serve as a vehicle for delivering the drug to a patient. Often the polymeric materials into which drugs are loaded are a part of or otherwise associated with implantable medical devices. For example, polymeric vascular catheters are commercially available with anti-infective agents loaded into the polymeric material forming the catheter body. The anti-infective agents prevent infection associated with implanting the catheters. In addition, it has been proposed that drug loaded polymeric boots to be disposed about implantable medical devices, such as cardiac defibrillators, infusion devices and implantable neurostimulators, may be similarly effective at preventing infection. However, the amount of drug that may be loaded into polymeric materials is currently limited.

BRIEF SUMMARY

It has been found that increased amounts of agents can be loaded into polymeric material that has been pre-extracted prior to loading.

In various embodiments, the invention provides a method. The method includes (i) contacting a polymeric material with a first solvent to produce a pre-extracted polymeric material, and (ii) contacting the pre-extracted material with a solution comprising one or more therapeutic agents and a second solvent to incorporate the therapeutic agents into the pre-extracted polymeric material. The first and second solvents are the same or different. The method may further include drying the pre-extracted polymeric material prior to contacting the pre-extracted polymeric material with the solution. Drying may occur at room temperature and ambient atmosphere for 2 hours or more (e.g., 12 hours or more). Drying may remove substantially all of the first solvent from the pre-extracted polymeric material. The polymeric material may be an elastomeric polymeric material. For example, the polymeric material may include silicone. The first solvent may be a non-polar solvent. For example, the first solvent may be as non-polar or more non-polar than ethyl acetate or may have a polarity index of 5.0 or less. The first solvent may be capable of increasing the weight of the polymeric material by 30% or more (e.g., 50% or more or 70% or more) after being in contact with the first solvent for two hours. In some instances, the first and second include butyl acetate. For example, first solvent may be butyl acetate and the second solvent may be an 85:15 mixture of butyl acetate and methanol. The one or more therapeutic agents may include one or more anti-infective agents. For example, the one or more anti-infective agents may include minocycline or rifampin.

Increasing the loading capacity of polymeric materials will increase the design flexibility of drug-loaded polymeric boots, sheaths, discs and the like. For example, the overall dimensions of the polymeric material may be reduced while still allowing for equivalent drug loading to larger polymeric materials. In addition, if it is desirable to more rapidly elute drug from the polymeric material, a thinner polymeric material (which will typically elute drug more rapidly than thicker material) may be used while still allowing for sufficient drug loading. These and other advantages will be readily understood from the following detailed descriptions when read in conjunction with the accompanying drawings.

DETAILED DESCRIPTION

Figure 1:
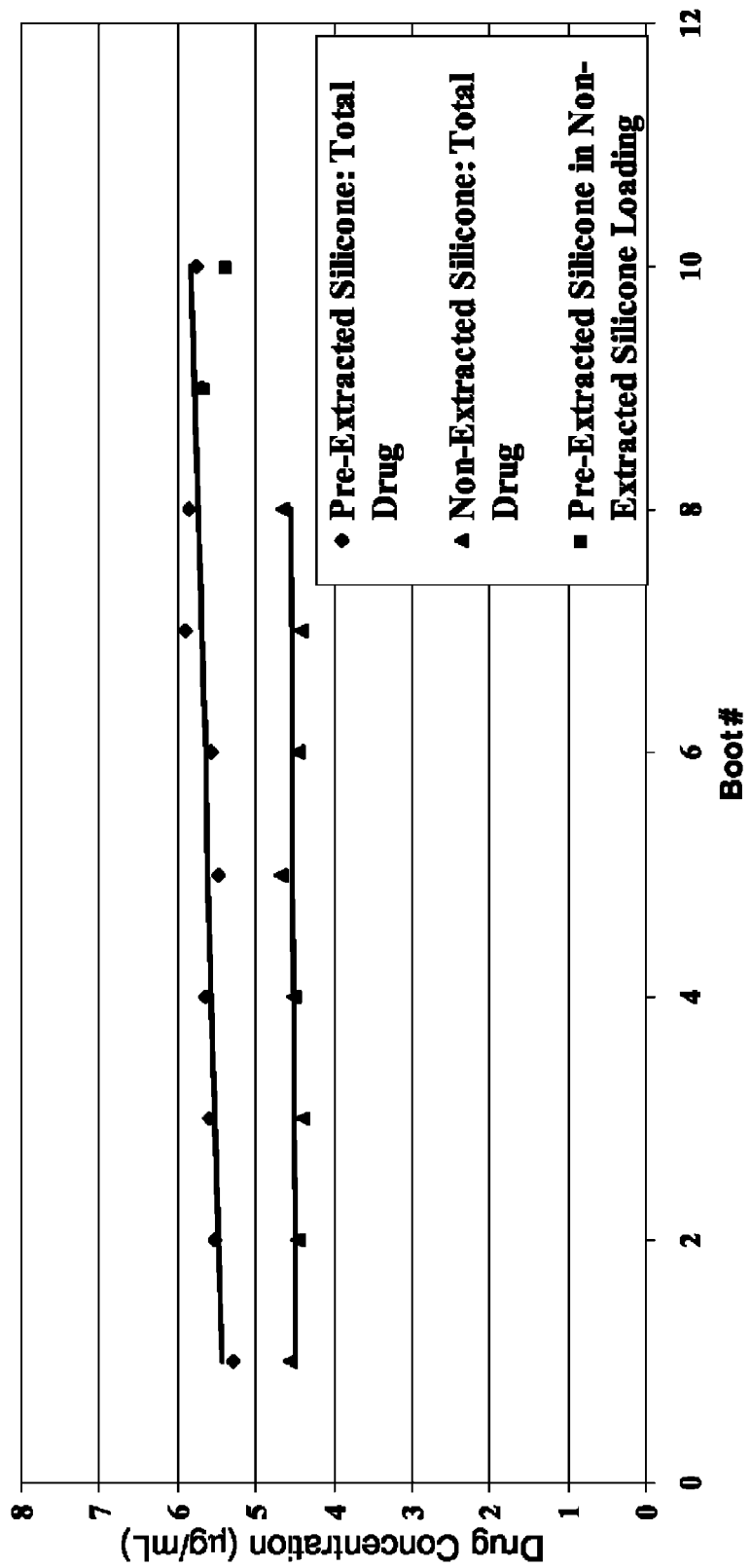
FIG. 1 is a graph of total drug (minocycline and rifampin) loaded in pre-extracted silicone boots and non-pre-extracted silicone boots.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "therapeutic agent" means a molecule, such as a large molecule (e.g., a peptide or nucleic acid or derivatives thereof) or a small molecule, that may result in a beneficial effect when administered to a subject, such as a human.

Reference herein to any chemical compound should be construed as reference to the compound and any pharmaceutically acceptable salts, solvates, hydrates, isomers, and polymorphs thereof.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure relates, among other things, to implantable medical devices, polymeric materials, and incorporation of agents into polymeric materials. It has been found that increased loading of agents into polymeric materials by solvent-mediated incorporation techniques occurs in polymeric material that has been pre-extracted. While not intended to be bound by theory, it is believed that the increased loading capacity of pre-extracted material may be at least partially due to removal of un-crosslinked monomers and oligomers from the polymeric material. It is further believed that solvents that are capable of swelling the polymeric material may serve to better extract oligomers and monomers than solvents that do not significantly swell the polymeric material. Thus, pre-extraction with solvents that swell the polymeric material may lead to increased subsequent loading of the polymeric material with therapeutic agent via a solvent-mediated loading process, regardless of whether the pre-extraction solvent is the same or different than the agent loading solvent.

Polymers

Any suitable polymeric material may be used in accordance with the teachings presented herein. The polymeric material may be any suitable shape and may take any suitable form. For example, the polymeric material may be in the form of a tube, sheath, sleeve, boot, disc, or the like. The polymeric material may be extruded, molded, or otherwise formed. Examples of commonly used suitable polymeric materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE).

The polymeric material may be biodegradable, such as synthetic or natural bioabsorbable polymers. Synthetic bioabsorbable polymeric materials that can be used to form the coating layers include poly(L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters) such as PEO/PLA, polyalkylene oxalates, polyphosphazenes, and polyarylates including tyrosine-derived polyarylates. According to another exemplary embodiment, the polymeric materials can be natural bioabsorbable polymers such as, but not limited to, fibrin, fibrinogen, cellulose, starch, collagen, and hyaluronic acid. "Biodegradable", "bioerodable", "bioabsorbable", and the like are used herein interchangeably.

In various embodiments, the polymeric material is an elastomeric polymeric material. Examples of elastomeric polymeric materials include polyisoprene, polyisobutylene, polystyrene, poly(vinyl chloride), polyurethane, silicone, ethylene-propylene elastomers, styrene-1,3-butadiene, acrylonitrile-1,3-butadiene, isobutylene-isoprene, and the like.

The polymeric material may be in the form of a boot designed to be placed around an implantable medical device or a disc, for example as described in U.S. Provisional Patent Application Ser. No. 60/912,234, entitled "REDUCTION OF INFECTION ASSOCIATED WITH MEDICAL DEVICE", filed on Apr. 17, 2007, which application is hereby incorporated herein by reference in its entirety to the extent that it does not conflict with the disclosure presented herein. The polymeric material with which one or more therapeutic agent has been associated may be placed in a subcutaneous pocket or may be placed on or about an implantable medical device. In various embodiments, the polymeric material is bonded, adhered to, coated on, or otherwise attached to the implantable medical device.

Therapeutic Agent

Any therapeutic agent may be associated with a polymeric material in accordance with the teachings presented herein. If a therapeutic agent loaded polymeric material is associated with an implantable medical device, it may be desirable to treat or prevent infections, inflammation, or proliferation associated with implantation of a medical device. Accordingly, it may be desirable to associate one or more anti-infective agent, one or more anti-inflammatory agent, one or more anti-proliferative agent, or a combination thereof with the polymeric material. In some circumstances, it may be desirable to deliver a local anesthetic. Additional therapeutic agents that may be associated with a polymeric material, regardless of whether the polymeric material is associated or to be associated with an implantable medical device, will be readily evident to one of skill in the art. A brief summary of some non-limiting classes of therapeutic agents that may be used follows.

1. Anti-Infective Agents

Any anti-infective agent may be used in accordance with various embodiments. As used herein, "anti-infective agent" means an agent that kills or inhibits the growth of an infective organism, such as a microbe or a population of microbes. Anti-infective agents include antibiotics and antiseptics.

A. Antibiotic

Any antibiotic suitable for use in a human may be used in accordance with various embodiments of the invention. As used herein, "antibiotic" means an antibacterial agent. Many antibiotics have limited effect against microbes other than bacteria. The antibacterial agent may have bacteriostatic and/or bacteriocidal activities.

Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

If the polymeric material is associated with or to be associated with an implantable medical device, it is desirable that the selected antibiotic(s) kill or inhibit the growth of one or more bacteria that are associated with infection following surgical implantation of a medical device. Such bacteria are recognized by those of ordinary skill in the art and include *Staphylococcus aureus, Staphylococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and micocycline is used. In an embodiment, a combination of rifampin and clindamycin is used.

B. Antiseptic

Any antiseptic suitable for use in a human may be used in accordance with various embodiments. As used herein, "antiseptic" means an agent capable of killing or inhibiting the growth of one or more of bacteria, fungi, or viruses. Many antiseptics, such as disinfectants, are effective against two or more of, or all of, bacteria, fungi, and viruses. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

If the polymeric material is associated with or to be associated with an implantable medical device (e.g., the polymeric material forms a part of the device, such as a catheter or lead, is to be disposed about, coated on, or otherwise adhered to the device, or is placed in proximity to the device after implantation), it is desirable that the antiseptic(s) selected kill or inhibit the growth of one or more microbe that are associated with infection following surgical implantation of a medical device. Such microbes are recognized by those of ordinary skill in the art and include *Staphylococcus aureus, Staphylococcus epidermis, Escherichia coli, Pseudomonas aureginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. In a particular embodiment, a combination of chlorohexidine and silver sulfadiazine is used.

C. Antiviral

Any antiviral agent suitable for use in a human may be used in accordance with various embodiments of the invention. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

D. Anti-Fungal

Any anti-fungal agent suitable for use in a human may be used in accordance with various embodiments of the invention. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that viruses will be killed or inhibited, it may be desirable to combine two or more anti-fungal agents. It may also be desirable to combine one or more antiseptics with one or more anti-fungal agent.

2. Anti-Inflammatory Agents

Any anti-inflammatory agent suitable for use in a human may be used in accordance with various embodiments. Non-limiting examples of anti-inflammatory agents include steroids, such as cortisone, hydrocortisone, prednisone, dexamethasone, methyl-prednisilone, an derivatives thereof, and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

3. Local Anesthetics

Any local anesthetic agent suitable for use in a human may be used in accordance with various embodiments. Non-limiting examples of local anesthetics agents include lidocaine, prilocaine, mepivicaine, benzocaine, bupivicaine, amethocaine, lignocaine, cocaine, cinchocaine, dibucaine, etidocaine, procaine, veratridine (selective c-fiber blocker) and articaine.

4. Other Pharmacological Agents

Non-limiting examples of other pharmacological agents that may be used include: beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin; Antineoplastic/antiangiogenic agents, such as antimetabolite agents, alkylating agents, cytotoxic antibiotics, vinca alkaloids, mitosis inhibitors, platinum compounds, tissue growth factor inhibitors, cisplatin and etoposide; Immunosuppressant agents, such as cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors; Anticoagulants, such as heparin and chondroitin sulfate; Platelet inhibitors such as ticlopidine; Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; Thrombolytic agents, such as stretokinase, urokinase and tissue plasminogin activators; Analgesics and antipyretics, such as the opioid analgesics such as buprenorphine, dextromoramide, dextropropoxyphene, fentanyl, alfentanil, sufentanil, hydromorphone, methadone, morphine, oxycodone, papavereturn, pentazocine, pethidine, phenopefidine, codeine dihydrocodeine; acetylsalicylic acid (aspirin), paracetamol, and phenazone; and Antiproliferative agents such as QP-2 (taxol), paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, and probucol; and combinations and/or derivates thereof.

In various embodiments, a steroid (e.g dexamethasone), a cell antiproliferative agent (e.g. rapamycin) and a radioactive substance are associated with a polymeric material.

A therapeutic agent may be present in the polymeric material at any suitable concentration. For example, a therapeutic agent may comprise 0.1% to 50%, 0.1% to 20%, 0.1% to 5%, 1% to 10%, etc. of the weight of the article.

Solvents

Any suitable solvent may be used to pre-extract the polymeric material and to load the therapeutic agent into the polymeric material. The pre-extraction solvent may be the same or different than the therapeutic agent loading solvent.

In general, it is believed that a solvent that is capable of swelling the polymeric material will serve as a better pre-extraction solvent than a solvent that is not capable of swelling the polymeric material. In various embodiments, the polymeric material is pre-extracted with a solvent that capable of increasing the weight of the polymer by 30% or more (e.g., 50% or more, 70% or more, or 100% or more) following two hours of submersion of the polymeric material in the solvent.

Of course, it will be understood that the appropriate solvent to obtain suitable swelling will depend on the polymeric material used.

In various embodiments, non-polar solvents are used to pre-extract the polymeric material. The non-polar solvent in various embodiments is at least as non-polar as ethyl acetate. Generally, alkane solvents, such as petroleum ethers, ligroin, and hexanes; aromatics, such as toluene and benzene; alkyl halides, such as tetrachloromethane and chloroform; and esters are at least as non-polar as ethyl acetate.

In various embodiments, solvents having a polarity index or 4.5 or less are used to pre-extract the polymeric material. Representative examples of solvents having a polarity index of 4.5 or less include benzene, n-butanol, butyl acetate, carbon tetrachloride, chloroform, 1,2-dichloroethane, cyclohexane, dichloromethane, ethyl acetate, methyl-t-butyl ether, pentane, n-propanol, toluene, trichloroethylene, xylene and tetrahydrofuran.

Non-polar solvents may be particularly well suited for pre-extraction of elastomeric polymeric materials, such as silicone polymeric material.

Any method may be used to pre-extract the polymeric material using the solvent. In various embodiments, the polymeric material is placed in contact with (e.g., submerged in) the solvent. The polymeric material may be submerged for an amount of time suitable to extract at least a portion of extractable material, such as un-crosslinked oligomers and monomers, from the polymeric material. For example, the polymeric material may be placed in the solvent for 1 minute to 24 hours or more (e.g., one hour or more, two hours or more, or three hours or more). The extraction may occur under any suitable temperature. In various embodiments, the pre-extraction occurs at room temperature. It will be understood that the temperature may be increased to increase the rate of extraction. In addition, the solvent in which the polymeric material is placed may be stirred or otherwise agitated to increase the rate of extraction.

Another suitable method may be to use a Soxhlet extractor, or the like. Briefly, the polymeric material containing extractables, such as oligomers and monomers, may be placed into a chamber that is placed onto a flask containing a solvent. The chamber is equipped with a condenser. The solvent is heated to reflux, and solvent vapor travels up a distillation arm and floods into the chamber housing the polymeric material. The chamber slowly fills with warm solvent, which can then dissolve the extractables. When the chamber almost fills, the solvent is emptied by a siphon side arm, with the solvent running back down to the distillation flask. The cycle may be repeated several times until a suitable amount of extractables have been removed from the polymeric material.

Following pre-extraction, the polymeric material may be dried. The polymeric material may be passively dried (e.g., ambient atmosphere at room temperature) or actively dried (e.g., blowing or heating). For example, the polymeric material may be left to dry at room temperature under ambient atmosphere conditions for two to twenty-four hours or more. In various embodiments, substantially all of the solvent is removed following pre-extraction.

Following pre-extraction, and optional drying, a therapeutic agent may be loaded into the polymeric material.

Any solvent-mediated process may be used to incorporate therapeutic agent into the polymeric material. For example, a therapeutic agent may be impregnated into the polymeric material by swelling the polymer in a solution of an appropriate solvent. Generally it is desirable that the therapeutic agent be soluble in the solvent and that the solvent is capable of swelling the polymer (e.g., as discussed above). One of skill in the art will readily understand which solvents are capable of dissolving the therapeutic agent and swelling the polymeric material. Regardless of the process or solvent used to incorporate or associate the therapeutic agent with the polymeric material, it is desired that the therapeutic agent be incorporated or associated in an amount effective to produce its intended therapeutic effect when administered to a subject.

As discussed below in the Example, loading may be substantially increased by pre-extraction. One advantage to increasing the loading capacity of a polymeric material is that the amount of agent loaded into the polymeric material may be better controlled. For example, in various embodiments, the polymeric material is partially loaded with therapeutic agent. To achieve partial loading, a variety of processes may be employed. For example, the concentration of therapeutic agent placed in the solvent may be controlled or the amount of time that the polymeric material is in contact with the therapeutic agent containing solvent may be controlled. Alternatively, or in addition, the therapeutic agent containing solvent may be sprayed on the polymeric material rather than placing the polymeric material in a solution containing the solvent and therapeutic agent. These and other suitable methods for controlling loading of therapeutic agent into polymeric material via a solvent-mediated process will be readily apparent to one of skill in the art.

EXAMPLES

Example 1

Increased Loading of Minocycline and Rifampin in Pre-Extracted Silicone

Increased capacity of silicone boots designed to fit snuggly around Restore® implantable neurostimulators (Medtronic, Inc.) to incorporate rifampin and minocycline was observed following pre-extraction of the boots with butyl acetate.
Drug Loading Procedure:
Molded, cured silicone (Dow-Q7 4850) boots designed to fit snuggly around Restore® implantable neurostimulators (Medtroinc, Inc.) were placed in a concentrated drug loading solution containing rifampin (30 mg/ml) and minocycline (15 mg/ml) in butyl acetate:methanol (85:15, by volume). The polymer was allowed to swell in this solution for one hour, rinsed and then dried overnight.
Effect of Pre-Extraction on Drug Loading:
The efficiency of various solvents to extract material from cured silicone was tracked by determining the weight loss post-extraction. Extraction with butyl acetate:methanol (85:15) gave the same average weight loss as did 100% butyl acetate. It was initially assumed that subjecting the polymer to drug loading should fulfill the same function as pre-extracting the material prior to drug loading. But, when pre-extracted material and non-extracted material from the same lot was drug-loaded, the pre-extracted polymer contained significantly higher drug concentrations. Minocycline concentration increased from 1.90 mg of drug per gram of polymer to 2.35 mg/g (20.5% increase); rifampin concentration increased from 2.61 mg/g to 3.28 mg/g (25.7%).
Solution Vs. Silicone Test Experiment:
One thought was that the existence of extractables in the loading solution might increase the solubility of the drugs in solution compared to solubility in the silicone, thus lowering the partitioning of drug into the silicone. Eight non-extracted silicone boots and 10 pre-extracted boots were drug loaded in separate loading solutions. Two additional pre-extracted silicone boots were then loaded in the formulation used to load the non-extracted boots. According to the hypothesis, the loading solution used for the non-extracted boots would theoretically contain higher levels of silicone extractables, and result in lower loading of the pre-extracted boots. The drug content results are shown in FIG. 1 and conclude that the higher concentration in the pre-extracted boots is due to a function of the pre-extracted silicone and not the extractables in the loading solution.
Solvent Swelling of Silicone Boots:
The effect of various solvents to swell (as determined by % weight increase) silicone boots was determined. Silicone boots were weighed, placed in a solvent for 2 hours, and weighed again. The results are presented in Table 1.

TABLE 1

Ability of various solvents to swell silicone polymeric material

| Solvent | % Weight Increase |
|---|---|
| THF | 105 |
| THF/water 87:13 | 38 |
| THF/ethanol 1:1 | 58 |
| THF/ethanol 4:1 | 92 |
| THF/ethanol 8:1 | 91 |
| THF/methanol 1:1 | 33 |
| THF/methanol 4:1 | 84 |
| Acetone | 15 |
| Acetone/ethanol 1:1 | 11 |
| Acteone/ethanol 4:1 | 8 |
| Acteone/ethanol 8:1 | 16 |
| Acetone/methanol 1:1 | 4 |
| Acetone/methanol 8:1 | 11 |
| THF/ethanol/water 70:25:5 | 34 |
| THF/ethanol/water 80:15:5 | 48 |
| THF/ethanol/water 90:5:5 | 66 |
| Toluene | 85 |
| Reagent alcohol (90:5:5) | 6 |
| Isopropyl alcohol | 13 |
| Ethyl acetate | 54 |
| Butyl Acetate | 73 |
| Cyclopentane | 62 |
| Cyclohexane | 85 |
| Chloroform | 166 |

The solvent ratios in Table 1 are by volume. The ability to swell silicone by 30% or more is believed to be suitable for increasing the loading capacity of silicone. The ability to swell silicone by 50% or more is believed to be more suitable for increasing the loading capacity of silicone.

Example 2

Increased Loading of Clonidine and Sulindac in Pre-Extracted Silicone

Increased capacity of sheets of silicone (Dow-Q7 4850) to incorporate clonidine and sulindac was observed following pre-extraction of the boots with butyl acetate.
Pre-Extraction:
Two of three sheets of 4850 silicone were extracted in butyl acetate (a sufficient amount to fully submerge a sheet). One sheet was removed after 2 hours; the other was removed after 24. The sheets were allowed to dry for 24 hours.
Clonidine and Sulindac Sample Preparation:
Nine 1¼ inch discs were punched from each sheet of silicone. The discs (27) were separated into 9 jars (3 per jar). Each jar contained a drug loading solution. Three jars contained clonidine, three contained dexamethasone and three contained sulindac. The nine non-extracted discs were divided equally into clonidine, dexamethasone and sulindac loading solutions, as were the 2 hr extracted and the 24 hour extracted discs.

Loading Solution Preparation:

Loading solutions contained: 4.5 mL anhydrous methanol, 1.35 g drug (clonidine or sulindac), and 25.5 mL butyl acetate. Because dexamethasone did not seem to dissolve well into this solution an extra 5 mL of methanol was added. However, this however did not appear to increase the solubility.

After stirring 24 hrs in solution, all the samples were removed, rinsed twice for approximately 10 seconds in a sufficient volume of methanol and allowed to dry overnight in open air on a drying rack. The samples were then stored until extraction in jars in a nitrogen purged foil bag.

Sample Extraction:

Each sample was cut in half, and the half sample was weighed. Initially only the clonidine and sulindac samples were analyzed. The results are presented in Table 2 below.

TABLE 2

Weight of half samples

| Description | Weight (mg) |
| --- | --- |
| Clonidine from non extracted polymer | 181.9 |
| Clonidine from non extracted polymer | 187.4 |
| Clonidine from non extracted polymer | 182.1 |
| Clonidine from 2 h extracted polymer | 195.8 |
| Clonidine from 2 h extracted polymer | 194.0 |
| Clonidine from 2 h extracted polymer | 189.5 |
| Clonidine from 24 h extracted polymer | 190.9 |
| Clonidine from 24 h extracted polymer | 190.1 |
| Clonidine from 24 h extracted polymer | 191.3 |
| Sulindac from non extracted polymer | 175.7 |
| Sulindac from non extracted polymer | 184.9 |
| Sulindac from non extracted polymer | 186.5 |
| Sulindac from 2 h extracted polymer | 195.5 |
| Sulindac from 2 h extracted polymer | 192.0 |
| Sulindac from 2 h extracted polymer | 188.7 |
| Sulindac from 24 h extracted polymer | 197.0 |
| Sulindac from 24 h extracted polymer | 199.0 |
| Sulindac from 24 h extracted polymer | 195.2 |

HPLC Analysis:

All samples were extracted in THF/ethanol 4:1 (15 mL) for 30 min; then re-extracted in THF/ethanol 4:1 (10 mL) for 20 min. The first and second extracts were combined in a volumetric flask and any additional volume was added to make exactly 25 mL of solution. These samples were stored in at 4° C. until analysis.

HPLC Analysis was performed using an Agilent 1100 stack. For dexamethasone, isocratic separation using acetonytrile:water (45:55) was performed. A Zorbax SB-Phenyl, 5 µm, 4.6×150 mm, column (Agilent Technologies, Inc.) was used at a column temperature of 30° C. The flow rate was 10 mL/min, with a run time of 15 minutes. Dexamethasone was detected by UV at 245 nm.

For sulindac, isocratic separation using 0.1% phosphoric acid in acetonitrile:water (38:62) was performed. A PRONTOSIL 120-5-C18-ace-EPS, 5 µm, 4.6×150 mm, column was used at a column temperature of 37° C. The autosampler temperature was 15° C. The flow rate was 1.0 mL/min, with a run time of 35 min. Sulindac was detected by UV at 285 nm. Injection volumes were 10-50 µL.

Figure 2:
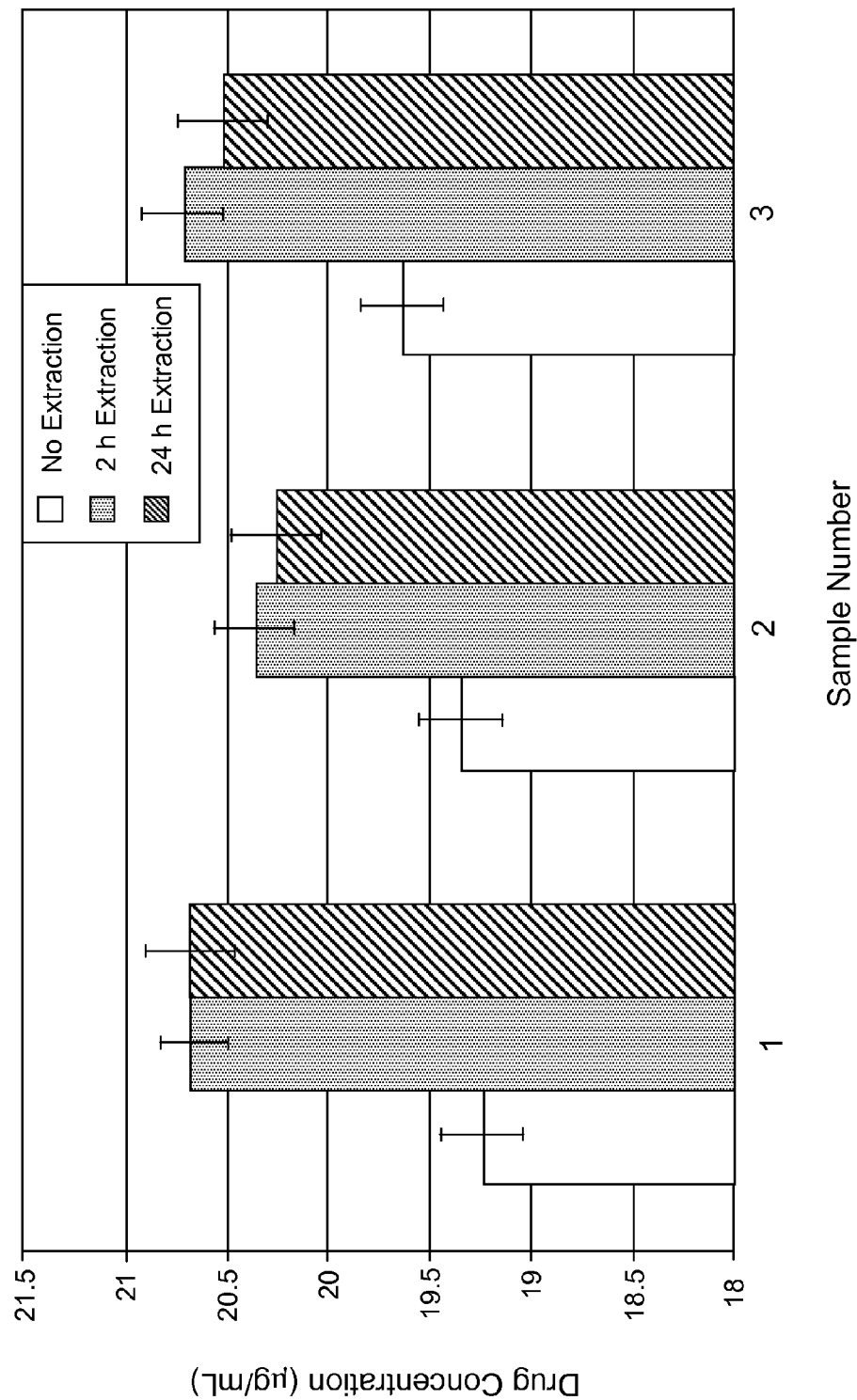
FIG. 2 is a graph of total drug (clonidine) loaded in pre-extracted silicone boots and non-pre-extracted silicone discs.

For clonidine, a Waters XBridge, 5 µm, 4.6×150 mm, column at a column temperature of 25° C. was used. The autosample temperature was ambient temperature. Isocratic separation using a mobile phase A (MPA):mobile phase B (MPB) ratio of 52:48 was employed. MPA consisted of 2.2 gm 1-octanesulfonic acid, sodium salt for each liter of nanopure water. MPB was HPLC Grade Methanol. The flow rate was 1 mL/min, with a run time of 15 minutes. Clonidine was detected by UV at 220 nm. The injection volume was 10 µL The results of the HPLC analysis for clonidine are presented in FIG. 2. An average of 19.41±0.20 µg/mL of clonidine was loaded into silicone discs that were not pre-extracted with butyl acetate. An average of 20.59±0.20 µg/mL of clonidine was loaded into silicone discs that were pre-extracted with butyl acetate for 2 hours. An average of 20.49±0.22 µg/mL of clonidine was loaded into silicone discs that were pre-extracted with butyl acetate for 24 hours. Accordingly, about a 6% increase in clonidine loading was observed in pre-extracted relative to non-extracted silicone discs. The difference between non-extracted and 2 hour extracted (p=0.006) and between non-extracted and 24 hour extracted (p=0.014), as well as non-extracted and extracted (2 hour plus 24 hour) (p=0.00004), was statistically significant. No significant difference was observed between 2 hour extracted and 24 hour extracted silicone (p=0.12).

Figure 3:
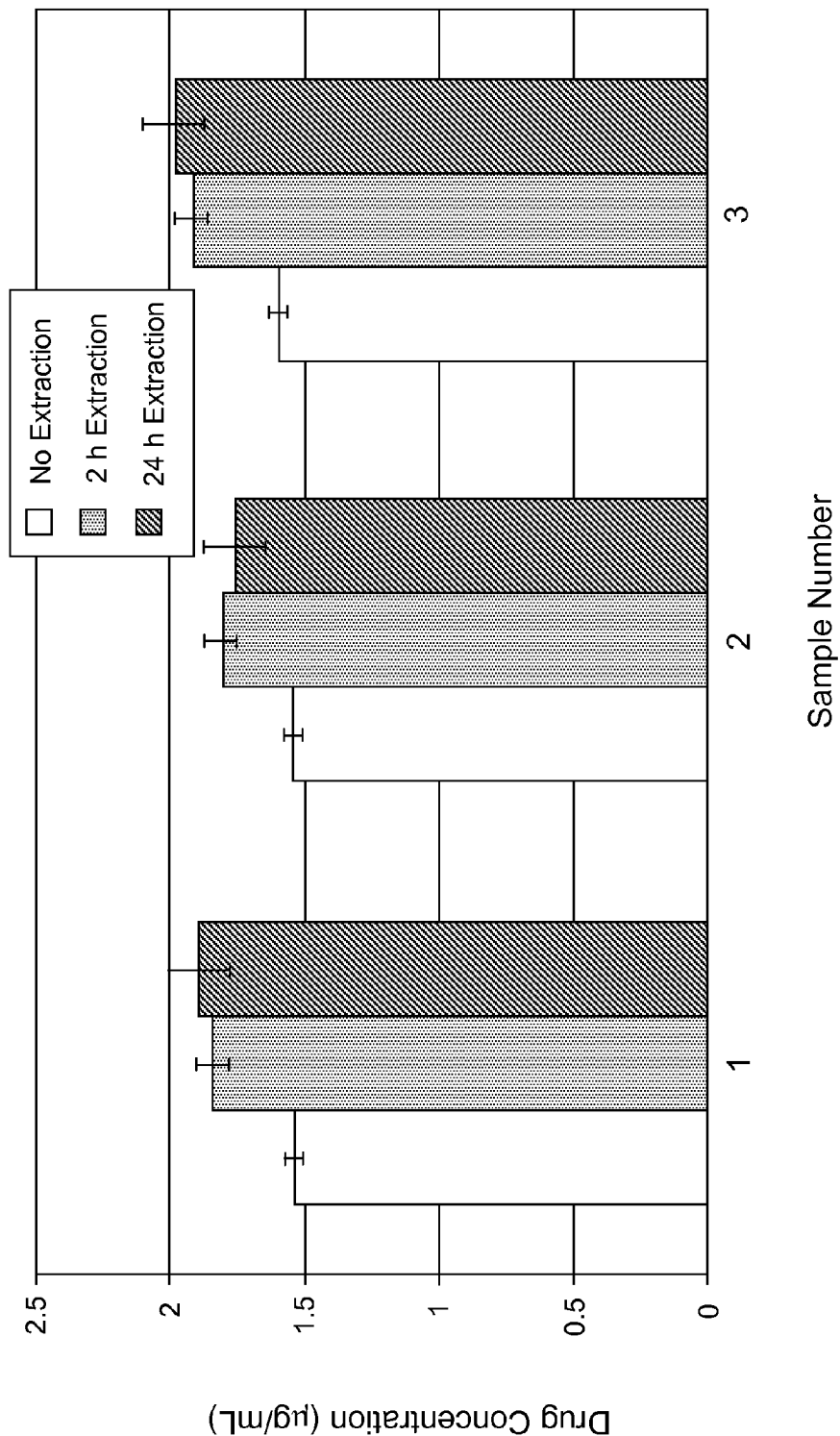
FIG. 3 is a graph of total drug (sulindac) loaded in pre-extracted silicone boots and non-pre-extracted silicone discs.

The results of the HPLC analysis for sulindac are presented in FIG. 3. An average of 1.56±0.03 µg/mL of sulindac was loaded into silicone discs that were not pre-extracted with butyl acetate. An average of 1.86±0.06 µg/mL of sulindac was loaded into silicone discs that were pre-extracted with butyl acetate for 2 hours. An average of 1.88±0.11 µg/mL of sulindac was loaded into silicone discs that were pre-extracted with butyl acetate for 24 hours. Accordingly, about a 19% increase in sulindac loading was observed in pre-extracted relative to non-extracted silicone discs. The difference between non-extracted and 2 hour extracted (p=0.0016) and between non-extracted and 24 hour extracted (p=0.013), as well as non-extracted and extracted (2 hour plus 24 hour) (p=0.0002), was statistically significant. No significant difference was observed between 2 hour extracted and 24 hour extracted silicone (p=0.31).

The results of the HPLC analysis for dexamethasone revealed no significant increase in drug loading as a result of pre-extraction. However, due to the substantial insolubility of dexamethasone in the solvent and the unsuccessful modification of the solvent to improve solubility, the results obtained from dexamethasone in this study are inconclusive at best.

Discussion:

In this study the hypothesis that more drug would load it to pre-extracted silicone was challenged with an extension of the loading time from 1 (for minocycline and rifampin study in Example 1) to 24 hours. Significant increases in drug loading were observed following a 24 hour loading time.

Thus, embodiments of INCREASED DRUG LOADING OF POLYMERIC MATERIAL are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   contacting a polymeric material consisting of silicone with a first solvent composition comprising butyl acetate to produce a pre-extracted silicone material, wherein the first solvent composition is free of antimicrobial agents;
   drying the pre-extracted silicone material to remove substantially all of the first solvent composition; and
   contacting the pre-extracted silicone material with a solution comprising one or both of minocycline and rifampin and a second solvent composition containing butyl acetate to incorporate the therapeutic agents into the pre-extracted polymeric material, wherein the first and second solvent compositions are the same or different, wherein the pre-extracted silicone material is free of minocycline and rifampin, and wherein the amount of the one or both of minocycline and rifampin incorporated into the pre-extracted polymeric material is greater than the amount of the one or both of the minocycline and rifampin that can be loaded into a control silicone polymeric material that has not been pre-extracted but that has been contacted with a solution comprising one or both of minocycline and rifampin under the same conditions as the pre-extracted polymeric material.

2. The method of claim 1, wherein the polymeric material is formed to have a shape.

3. The method of claim 2, wherein the polymeric material is a boot configured to be placed about an implantable medical device.

4. The method of claim 2, wherein the polymeric material is a disc or sheet.

5. The method of claim 1, wherein the first solvent composition has a polarity index of 4.5 or less.

6. The method of claim 1, wherein the first solvent composition consists essentially of butyl acetate.

7. The method of claim 1, wherein the first solvent composition is as non-polar or more non-polar than ethyl acetate.

8. The method of claim 1, wherein the first solvent composition has a polarity index of 5.0 or less.

9. The method of claim 1, wherein the first solvent composition is capable of increasing the weight of the polymeric material by 30% or more following two hours of submersion of the polymeric material in the first solvent composition.

10. The method of claim 1, wherein the first solvent composition is capable of increasing the weight of the polymeric material by 50% or more following two hours of submersion of the polymeric material in the first solvent composition.

11. The method of claim 1, wherein the first solvent composition is capable of increasing the weight of the polymeric material by 70% or more following two hours of submersion of the polymeric material in the first solvent composition.

12. The method of claim 1, wherein the first solvent composition is butyl acetate and the second solvent composition is a 85:15 mixture of butyl acetate and methanol.

* * * * *